United States Patent [19]

Lau et al.

[11] Patent Number: 5,262,284
[45] Date of Patent: Nov. 16, 1993

[54] ARYLIDENE PYRAZOLONE COUPLER

[75] Inventors: Philip T. S. Lau; Danny R. Thompson, both of Rochester; Stephen P. Singer, Spencerport, all of N.Y.

[73] Assignee: Eastman Kodak Company, Rochester, N.Y.

[21] Appl. No.: 731,220

[22] Filed: Jul. 15, 1991

[51] Int. Cl.$^5$ .................. G03C 7/384; G03C 7/333
[52] U.S. Cl. .................. 430/359; 430/504; 430/517; 430/522; 430/554; 430/555; 430/549; 430/559
[58] Field of Search .......... 430/359, 504, 507, 510, 430/517, 522, 554, 555, 549, 559

[56] References Cited

U.S. PATENT DOCUMENTS

| | | | |
|---|---|---|---|
| 2,688,538 | 9/1954 | Ganguin et al. | 430/359 |
| 2,688,540 | 9/1954 | Ganguin et al. | 430/359 |
| 2,688,541 | 9/1954 | Ganguin et al. | 430/559 |
| 4,234,677 | 11/1980 | Postle | 430/517 |
| 4,311,787 | 1/1982 | Lemahieu et al. | 430/522 |
| 4,659,651 | 4/1987 | Yagihara et al. | 430/542 |
| 4,883,746 | 11/1989 | Shimada et al. | 430/504 |
| 4,923,789 | 5/1990 | Yagihara et al. | 430/517 |
| 4,968,594 | 11/1990 | Shimazaki et al. | 430/549 |

FOREIGN PATENT DOCUMENTS

| | | | |
|---|---|---|---|
| 0252550 | 1/1988 | European Pat. Off. | 430/507 |
| 3052138 | 3/1988 | Japan | 430/549 |
| 168995 | 11/1965 | U.S.S.R. | 430/504 |
| 968461 | 9/1964 | United Kingdom . | |

*Primary Examiner*—Lee C. Wright
*Attorney, Agent, or Firm*—Gordon M. Stewart

[57] ABSTRACT

A photographic element including a support bearing a silver halide photographic emulsion and an image dye-forming coupler, wherein the image dye-forming coupler includes a ballasted arylidene pyrazolone which is also a filter dye that upon exposure and processing of the element is destroyed in both exposed and unexposed areas of said element or a masking coupler that upon exposure and processing is destroyed only in exposed areas of the element. The arylidene pyrazolone compound includes an oxygen-inclusive electron donating group in conjugation with the arylidene function, preferably positioned para to the arylidene function.

15 Claims, No Drawings

ARYLIDENE PYRAZOLONE COUPLER

BACKGROUND OF THE INVENTION

The present invention relates to an image dye-forming coupler which also functions as a filter dye or a masking coupler. In particular, it relates to an arylidene pyrazolone image dye-forming coupler.

A color photographic material based on the subtractive color process system conventionally includes at least one blue-sensitive silver halide emulsion layer containing at least one yellow image dye-forming coupler, at least one green-sensitive silver halide emulsion layer containing at least one magenta image dye-forming coupler and at least one red-sensitive silver halide emulsion layer containing at least one cyan image dye-forming coupler. It is well known to employ filter dyes or layers in such multilayer color photographic materials to prevent exposure of underlying light-sensitive silver halide emulsion layers to light having a wavelength which is absorbed undesirably by the underlying light-sensitive emulsion layer. This problem with undesired absorption by the silver halide emulsion layers is especially significant with respect to blue light since the natural silver halide sensitivity is to blue light, regardless of whether the silver halides are sensitized to other colors such as green or red.

A yellow filter dye, therefore, typically is incorporated in the photographic material above the green- and/or red-sensitive emulsion layers in order to absorb the undesired blue light during exposure of the photographic material. To avoid the unwanted presence of a high blue $D_{min}$ after processing, however, the yellow filter dyes should be capable of removal and/or decolorization during processing of the photographic material.

Conventionally, filter dyes and image dye-forming couplers are separate compounds. This results in the disadvantage of requiring the production of numerous different compounds and increases the manufacturing problems associated with incorporating a large number of compounds and/or layers in a color photographic material.

U.S. Pat. Nos. 2,688,538, 2,688,540 and 2,688,541 and United Kingdom Patent Specification No. 968,461 disclose a styryl dye formed from a pyrazolone magenta dye-forming coupler parent which includes a substituted or unsubstituted amino group in a position on the benzene ring para to the methylene group. The amino group, however, prevents these dyes from undergoing rapid decolorization during processing.

U.S. Pat. No. 4,311,787 discloses a class of arylidene pyrazolone compounds which act only as classic filter dyes rather than as filter dye/image dye-forming couplers. These filter dyes do not function as image dye-forming couplers because, among other reasons, they wash out of the photographic film into the developer since they do not include ballast groups.

It is also well known to utilize a masking coupler in photographic materials for color correction of the undesirable side-absorption tendencies of the cyan, magenta and yellow dye images. For example, the conventional masking technique for use with a magenta dye is to employ a colored magenta dye forming coupler, i.e., a masking coupler, which is colored (yellow) so that it has an absorption in the unwanted blue region.

SUMMARY OF THE INVENTION

It is therefore an object of the present invention to provide a compound which functions as both an image-forming coupler and a filter dye. The filter dye should be colored as coated and then decolorize in both the exposed and unexposed areas during processing.

It is also an object of the present invention to provide a masking coupler which has the same generic structure as the filter dye/image dye-forming couplers.

In accomplishing the foregoing objects there is provided according to the present invention a photographic element comprising a support bearing a silver halide photographic emulsion and an image dye-forming coupler, wherein the image dye-forming coupler is a ballasted arylidene pyrazolone which is also a filter dye that upon exposure and processing of the element is destroyed in both exposed and unexposed areas of the element or a masking coupler that upon exposure and processing is destroyed in only the exposed areas of the element. The arylidene pyrazolone has a generic chemical structure represented by formula A:

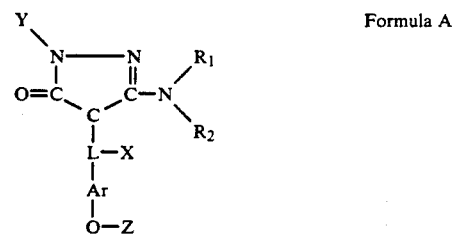

Formula A wherein L is an alkenyl or alkadienyl group, preferably methine, and Ar is a substituted aromatic group having the —O—Z group in conjugation with L, preferably positioned para to L, and optionally having additional substituents;

X is a hydrogen atom, a branched or unbranched aliphatic group or a heterocyclic ring formed with Ar;

Y is an unsubstituted aryl group, or an aryl or pyridyl group substituted with at least one substituent selected from the group consisting of a halogen atom and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl and trifluoromethyl groups;

Z is a hydrogen atom, an alkyl group, an aryl group, or an arylalkyl group;

$R_1$ and $R_2$ are the same or different and are each independently a hydrogen atom, a substituted or unsubstituted aromatic group, a branched or unbranched aliphatic group, a heterocyclic group, a substituted or unsubstituted aromatic or aliphatic carbonyl group, a substituted or unsubstituted aromatic or aliphatic sulfonyl group, or a substituted or unsubstituted aromatic or aliphatic sulfamoyl group; and at least one of Ar, X, Y, Z, $R_1$ and $R_2$ includes a ballast group which renders the arylidene pyrazolone substantially immobile.

Further objects, features and advantages of the present invention will become apparent from the detailed description of preferred embodiments that follows.

DETAILED DESCRIPTION OF THE PREFERRED EMBODIMENTS

According to a first embodiment of the present invention, there is provided an arylidene pyrazolone compound which exhibits the dual functionality of an image dye-forming coupler and a filter dye. This embodiment also is referred to in the application as the "image dye-forming coupler/filter dye" embodiment. Specifically, the image dye-forming coupler/filter dye compound typically is yellow-colored as coated in a color photographic material, produces a magenta dye imagewise upon exposure and processing, and leaves no residual yellow color in the unexposed areas after processing. The yellow color of the compound as coated acts to absorb blue light during exposure, thus protecting the silver halide emulsion layers underlying and/or associated with the coated compound. Utilization of the present compound in place of, or in addition to, conventional magenta image dye-forming couplers dispenses with the need for a separate yellow filter dye and/or yellow filter layer. That is to say, the net effect of using the present compound is reduced coating layers and chemical load in the photographic element.

Another advantage is that removal or washing out of the present filter dye from the color photographic material during processing is not required. Conventional filter dyes, which would remain colored after processing, must be washed out to prevent color distortion, i.e., high $D_{min}$, in the resulting print. Ballast groups, therefore, cannot be attached to conventional filter dyes since they would prevent the dyes from washing out of the film. Without ballast groups, however, it is difficult to maintain conventional filter dyes in the proper film layer since they have a tendency to wander between film layers.

In the present invention, however, the color of the filter dye as coated is destroyed during processing. Washing out of the present filter dyes, therefore, is unnecessary, thereby allowing the attachment of ballast groups to the dye molecule.

The ballast group can be attached to the portion of the compound of formula A which forms the image dye upon reaction with oxidized developer, i.e., the ballast group can be part of Y, $R_1$ and/or $R_2$. In this embodiment, the resulting image dye will be immobile. The ballast group also can be attached to the coupling-off portion or group of the present filter dye, i.e., the ballast group can be part of X, Ar and/or Z. The resulting image dye then is free to wander, improving granularity in the developed exposure, and the residual uncoupled compound formed from the coupling-off portion is immobile, remaining in the film and avoiding contamination of the developer solution.

According to a second embodiment of the present invention, there is provided a novel arylidene pyrazolone masking coupler which has the same generic structure as the image dye-forming coupler/filter dye. In this embodiment, the arylidene pyrazolone compound is not prone to decolorization during processing and remains colored in the nonexposed area of the film after development. Specifically, the compound reacts with oxidized developer to form a magenta dye in the areas of exposure but does not undergo decolorization in the areas of nonexposure.

The difference between the first and second embodiments lies primarily in the arylidene group. Generally, if Ar in formula A represents phenyl, the compound acts as an image dye-forming coupler/filter dye. On the other hand, if Ar represents a naphthyl or higher aromatic ring group, the compound acts as a masking coupler. Extending the number of $C_6$ rings in Ar, such as, for example, in a biphenylyl group, tends to prevent decolorization of the compound.

In both the image dye-forming coupler/filter dye and masking coupler embodiments Ar is substituted with an oxygen-inclusive electron donating group, —O—Z, that is in conjugation with the double bond of L. In other words, the electron donating group can be positioned ortho or, more preferably, para to the arylidene function. It follows that an electron withdrawing group should not be in the para or ortho position of the arylidene group. Similarly, a substituted or unsubstituted amino group should not be positioned ortho or para to the arylidene function since it would prevent decolorization of the filter dye.

Preferred electron donating groups include alkoxy, aryloxy and arylalkoxy groups. Especially advantageous is a hydroxy group. Other groups, such as a substituted or unsubstituted sulfonamido group, that act as electron-donating groups are also usable.

Ar in both the image dye-forming coupler/filter dye and the masking coupler embodiments can also include substituents at the meta and/or ortho positions of the ring attached via L to the pyrazolone. The naphthyl or higher aromatic ring of the masking coupler can be substituted at any position. Examples of such substituents include hydroxy, alkoxy, heterocyclic, branched or unbranched aliphatic groups and halogen atoms. Particularly preferred are electron withdrawing groups at the meta position with respect to the arylidene. Examples of such electron withdrawing groups include carbamoyl, sulfamoyl, sulfonyl, nitro and azo groups.

L in formula A represents an alkenyl or alkadienyl group such as methine or a vinyl group. Preferably, L is a methine group.

X in formula A preferably represents a hydrogen atom. X may also represent a branched or unbranched aliphatic group or a heterocyclic ring formed with Ar.

The present compound typically is produced from a conventional magenta image dye-forming parent coupler moiety as described in detail below. The phrase "parent coupler moiety" means the portion of the compound represented in formula A which does not include the arylidene group. Y, $R_1$ and $R_2$, therefore, preferably represent groups which, along with the pyrazolone group, comprise such a conventional coupler.

In particular, Y represents an unsubstituted aryl group, or an aryl or pyridyl group substituted with at least one substituent selected from the group consisting of a halogen atom and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl and trifluoromethyl groups, preferably a 2,4,6-trichlorophenyl group or a 2,5- or 2,6-disubstituted aryl group. $R_1$ and $R_2$ represent a hydrogen atom, a substituted or unsubstituted aromatic group, a branched or unbranched aliphatic group, a heterocyclic group, a substituted or unsubstituted aromatic or aliphatic carbonyl group, a substituted or unsubstituted aromatic or aliphatic sulfonyl group, or a substituted or unsubstituted aromatic or aliphatic sulfamoyl group. In preferred embodiments $R_1$ represents a hydrogen atom and $R_2$ represents a substituted aromatic group or a substituted aromatic carbonyl group. Advantageously, the total number of carbon atoms in $R_1$ and $R_2$ combined is at least 6.

In general, the arylidene group acts as a timing group as described, for example, in U.S. Pat. No. 4,912,024 and is joined to the parent coupler moiety at any of the positions from which groups released from couplers by reaction with oxidized color developing agent can be attached. Preferably, the arylidene group is attached at the coupling position of the parent coupler moiety so that upon reaction of the present compound with oxidized developer agent the arylidene group will be displaced. The arylidene group is released from the parent coupler moiety by means of an intramolecular electron transfer reaction via the alkylenic conjugated chain as described, for example, in U.S. Pat. No. 4,959,299.

Particularly preferred parent coupler moieties are represented by the following formulas, wherein the asterisk denotes the position of the arylidene group according to the present invention:

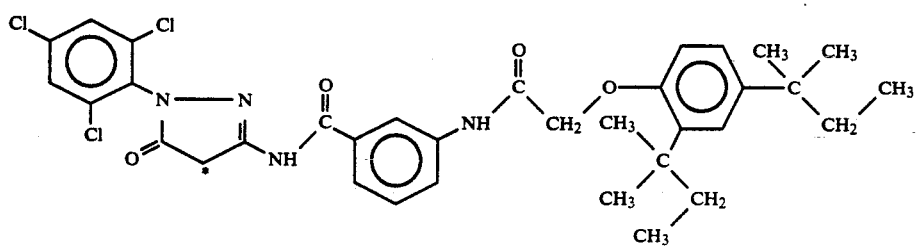

Formula B

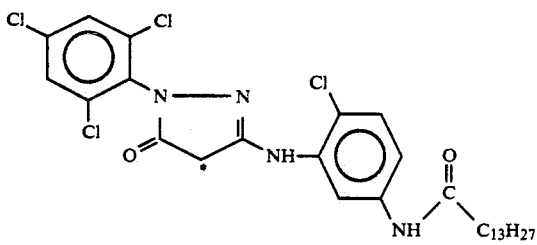

Formula C

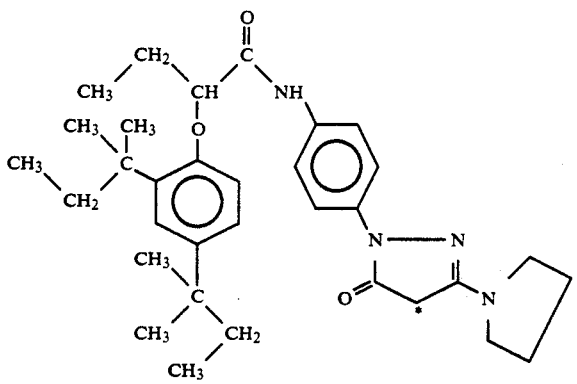

Formula D

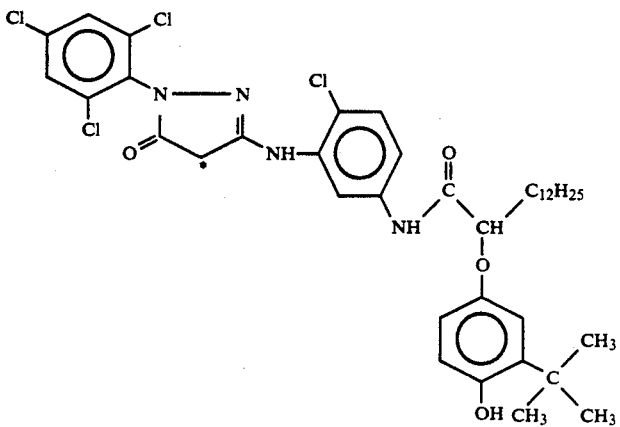

Formula E

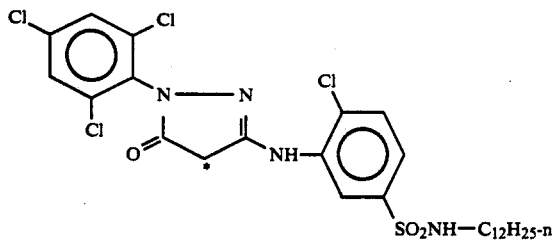

Formula F

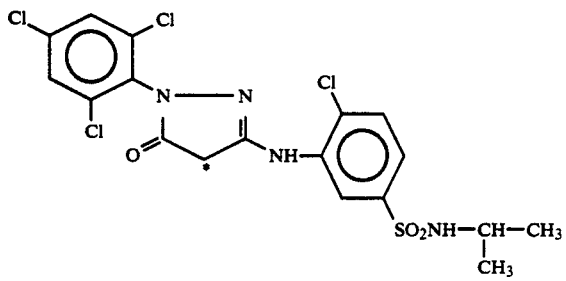

Formula G

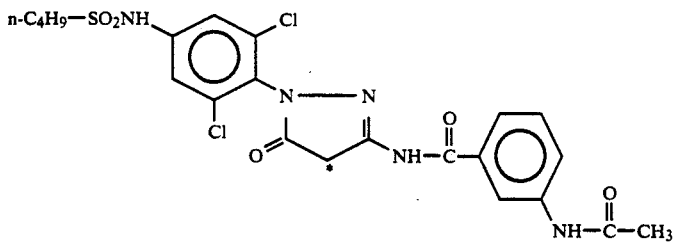

Formula H

Of these, parent coupler moieties B and C are especially advantageous.

As described previously, the present compound includes at least one ballast group which renders it substantially immobile. In other words, at least one of Ar, X, Y, Z, $R_1$ and $R_2$ includes a group of such molecular size and configuration as to render the present compound nondiffusible as described, for example, in U.S. Pat. Nos. 4,420,556 and 4,923,789. Advantageous ballast groups include alkyl and aryl groups having from about 8 to 32 carbon atoms.

The present compound also can include at least one solubilizing group such as, for example, a carboxyl, sulfonic or sulfonamide group, to effect the reactivity of the compound and assist the diffusion of the image dye in the film. Prior to processing, the present arylidene pyrazolone is part of an oil droplet. Due to the presence of the ballast group, the compound tends to be buried within the oil droplet, thereby inhibiting the reaction of the compound with materials in aqueous phase, such as oxidized developer. The solubilizing group drives the compound towards the surface of the oil droplet where it is available for reaction with materials in aqueous phase.

When diffusion of the image dye resulting from reaction of the present arylidene pyrazolone with oxidized developer is desired, it is advantageous to include solubilizing groups on the parent coupler or image dye-forming moiety. Diffusion of the image dye can be controlled by balancing the number and strength of solubilizing groups and the number and/or size of mini-ballast groups that can be attached to the parent coupler moiety. The term "mini-ballast" groups as used herein denotes an aliphatic or aromatic group having about 2 to 6 carbon atoms.

It is presumed that the image dye-forming coupler/filter dye is destroyed (i.e., decolorized) in the unexposed areas upon processing through a Michael reaction with the aniline compound or compounds present in the developer solution. The mechanism of a Michael reaction is well known and is described, for example, in House, *Modern Synthetic Reactions*, pp. 595-623 (pub. by W. A. Benjamin, 2d ed. 1972). Due to the extended chromophore, the masking coupler embodiment does not undergo a Michael reaction and thus retains its color in the unexposed areas.

In the exposed areas of the film the present compound typically forms a magenta dye image in the presence of oxidized developer. The compound may react directly with oxidized developer or, more likely, it undergoes disproportionation and/or hydrolysis to form intermediates which then react with the oxidized developer.

The arylidene pyrazolone compound according to the present invention can be incorporated into photographic elements by conventional methods Photographic elements according to the invention can be processed by conventional techniques in which color forming couplers and color developing agents are incorporated in separate processing solutions or compositions or in the element itself.

Photographic elements in which the compound according to the invention are incorporated can be simple single color elements comprising a support and a single silver halide emulsion layer, or they can be multilayer, multicolor elements. Multicolor elements contain dye image-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders known to those skilled in the art. In an alternative format, the emulsions sensitive to each of the three primary regions of the spectrum can be disposed as a single segmented layer, e.g., as by the use of microvessels as described in Whitmore, U.S. patent application Ser. No. 184,714, filed Sep. 8, 1980, now issued as U.S. Pat. No. 4,362,806.

The compounds according to the invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated therewith other photographic coupler compounds such as competing couplers. These other photographic couplers can form dyes of the same or different color and hue as the compounds according to the invention. In addition, the silver halide emulsion layers and other layers of the photographic element can contain other conventional additives.

A typical multilayer, multicolor photographic element can comprise a support having thereon a red-sensitive silver halide emulsion unit having associated therewith a cyan dye image-forming material, a green-sensitive silver halide emulsion unit having associated therewith a magenta dye image-forming material, and a blue-sensitive silver halide emulsion unit having associated therewith a yellow dye image-forming material. Each silver halide emulsion unit can comprise one or more layers. The various units and layers moreover can be arranged in different locations with respect to one another.

The masking coupler embodiment according to the present invention preferably is incorporated in the green-sensitive silver halide emulsion layer. The image dye-forming coupler/filter dye preferably is incorporated in the layers located the greatest distance from the film support layer. It is often advantageous to divide each particularly sensitized silver halide emulsion unit into a plurality of layers having decreasing sensitivity as the layers approach the film support. In this case, the image dye-forming coupler/filter dye is located in the more sensitive layers away from the film support.

A typical multicolor photographic element can also contain additional layers, such as interlayers, overcoat layers, subbing layers and the like.

The light-sensitive silver halide emulsions can include coarse, regular or fine grain silver halide crystals or mixtures thereof. The silver halides employed in the present invention generally can comprise any light-sensitive silver halides known in the photographic art such as, for example, silver chloride, silver bromide, silver bromoiodide, silver chlorobromoiodide and mixtures thereof. The emulsions can be negative-working or direct-positive. They can form latent images predominantly on the surface of the silver halide grains or predominantly on the interior of the silver halide grains. They can be chemically and spectrally sensitized. The emulsions typically will be gelatin emulsions although other hydrophilic colloids are also useful.

Tabular grain silver halide emulsions can also be utilized in the photographic element of the present invention. In general, tabular grain emulsions are those in which greater than 50 percent of the total grain projected area comprises tabular grain silver halide crystals having a grain diameter and thickness selected so that the diameter divided by the mathematical square of the thickness is greater than 25, wherein the diameter and thickness are both measured in microns. An example of tabular grain emulsions is described in U.S. Pat. No. 4,439,520.

Preferably, the compounds according to the invention are incorporated in silver halide emulsions and the emulsions coated on a support to form a photographic element. Alternatively, the inventive compounds can be incorporated in photographic elements adjacent the silver halide emulsion where, during development, the compounds will be in reactive association with development products such as oxidized color developing agent. Thus, as used herein, the term "associated therewith" signifies that the compound is in a silver halide emulsion layer or in an adjacent location where, during processing, it will come into reactive association with silver halide development products.

The support can be any support used with photographic elements. Typical supports include cellulose nitrate film, cellulose acetate film, polyvinylacetal film, polyethylene terephthalate film, polycarbonate film and related films or resinous materials, as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylenebutene copolymers and the like.

In the following discussion of suitable materials for use in the emulsions and elements according to the invention, reference will be made to *Research Disclosure*, Dec. 1989, Item 308119, published by Kenneth Mason Publications Ltd., Emsworth, Hampshire P010 7DQ, U.K., the disclosures of which are incorporated in their entireties herein by reference. This publication will be identified hereafter as "Research Disclosure".

The silver halide emulsions employed in the elements according to the invention can be either negative-working or positive-working. Suitable emulsions and their preparation are described in Research Disclosure Sections I and II and the publications cited therein. Suitable vehicles for the emulsion layers and other layers of elements according to the invention are described in Research Disclosure Section IX and the publications cited therein.

In addition to the compounds according to the invention, the elements according to the invention can include additional couplers as described in Research Disclosure Section VII, paragraphs D, E, F and G and the Publications cited therein. These couplers can be incorporated in the elements and emulsions as described in Research Disclosure Section VII, paragraph C and the publications cited therein.

The photographic elements according to the invention, or individual layers thereof, can contain brighteners (see Research Disclosure Section V), antifoggants and stabilizers (see Research Disclosure Section VI), antistain agents and image dye stabilizers (see Research Disclosure Section VII, paragraphs I and J), light-absorbing and scattering materials (see Research Disclosure Section VIII), hardeners (see Research Disclosure Section X), plasticizers and lubricants (see Research Disclosure Section XII), antistatic agents (see Research Disclosure Section XIII), matting agents (see Research Disclosure Section XVI), and development modifiers (see Research Disclosure Section XXI).

The photographic elements according to the invention can be coated on a variety of supports as described in Research Disclosure Section XVII and the references cited therein.

Photographic elements can be exposed to actinic radiation, typically in the visible region of the spectrum, to form a latent image as described in Research Disclosure Section XVIII, and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylenediamines. Especially preferred are 4-amino-N,N-diethylaniline hydrochloride, 4-amino-3-methyl-N,N-diethylaniline hydrochloride, 4-amino-3-methyl-N-ethyl-N-β-(methanesulfonamido)ethylaniline sulfate hydrate, 4-amino-3-β-(methanesulfonamido)ethyl-N,N-diethylaniline hydrochloride and 4-amino-N-ethyl-N-(2-methoxyethyl)-m-toluidinedi-p-toluenesulfonic acid.

With negative-working silver halide this processing step leads to a negative image. To obtain a positive (or reversal) image, this step can be preceded by development with a non-chromogenic developing agent to develop exposed silver halide, but not form dye, then uniformly fogging the element to render unexposed silver halide developable, followed by development with a chromogenic developer. Alternatively, a direct-positive emulsion can be employed to obtain a positive image.

Development is followed by the conventional steps of bleaching, fixing, or bleach-fixing, to remove silver and silver halide, washing and drying.

The arylidene pyrazolone compounds according to the present invention can be prepared by methods known in the organic synthesis arts. Typically, they are prepared according to the following exemplary scheme:

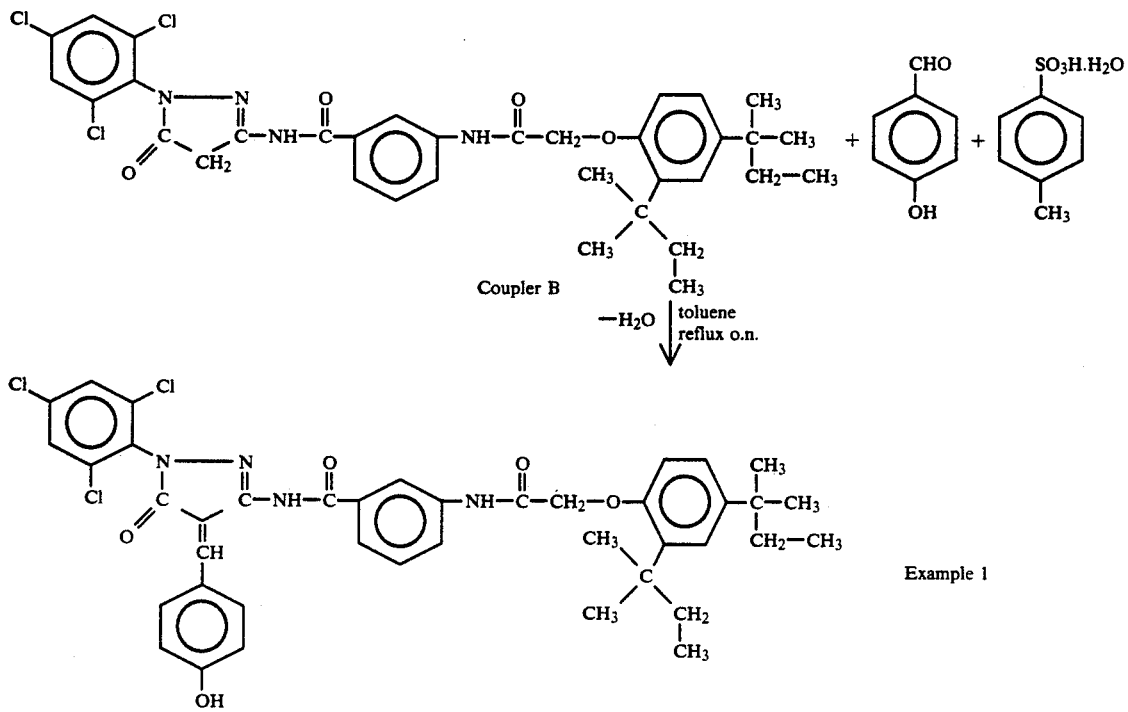

A 500 ml single-necked reaction flask was charged with 1.72 g (0.01 mol) of p-toluenesulfonic acid hydrate and 275 ml of toluene which previously had been stored over a molecular sieve. The flask was fitted with a Dean-Stark moisture trap, a magnetic stirrer and reflux condenser. The toluene was heated to reflux briefly in order to remove any residual water and dehydrate the acid hydrate. The solution was allowed to cool briefly and a mixture of 67.20 g (0.10 mol) of coupler B and 13.43 g (0.11 mol) of 4-hydroxybenzaldehyde was added to the warm, stirred toluene/p-toluenesulfonic acid mixture. The reaction mixture was held under reflux while water was collected. After two hours about 2 ml of water had been collected and after six hours a bright red-colored precipitate formed. Reflux was continued overnight. The next day the solution was filtered hot and 40 g of red-orange crystals collected. The crude benzylidene compound was triturated with ethyl acetate to give an essentially orange product. The product was recrystallized from a mixture of acetonitrile and tetrahydrofuran. Total yield was 27.5 g with a melting point of 244°–245° C. The structure of the product was consistent with its NMR spectrum and elemental analysis.

Using a similar synthesis procedure, compounds represented by formula A can be prepared wherein Ar—O—Z is, for example:

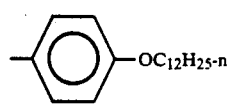

Example 2

-continued
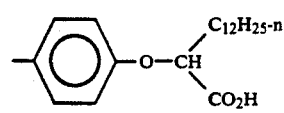  Example 3
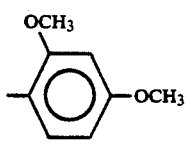  Example 4
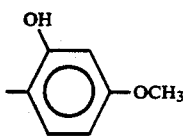  Example 5
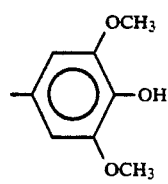  Example 6
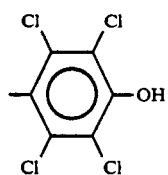  Example 7
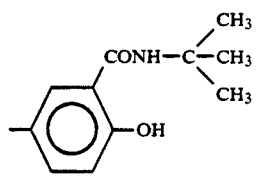  Example 8
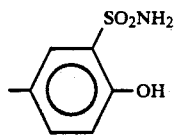  Example 9
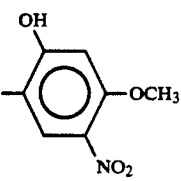  Example 10
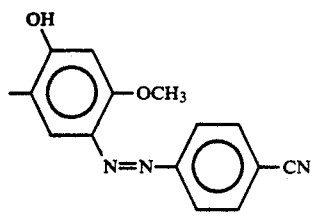  Example 11
-continued
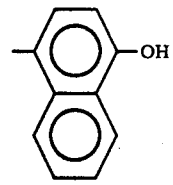  Example 12
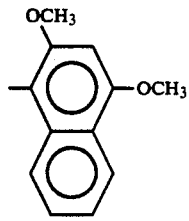  Example 13
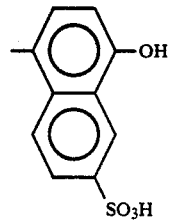  Example 14
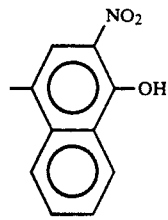  Example 15
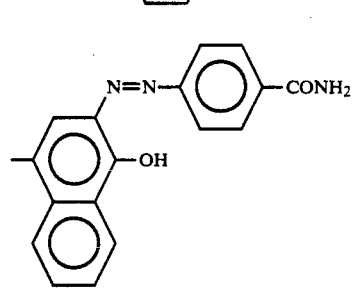  Example 16
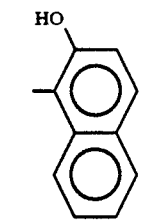  Example 17
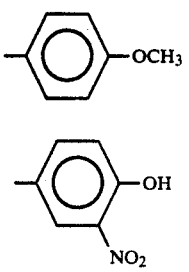  Example 18
Example 19

Preferred compounds include, in addition to Example 1, the following:
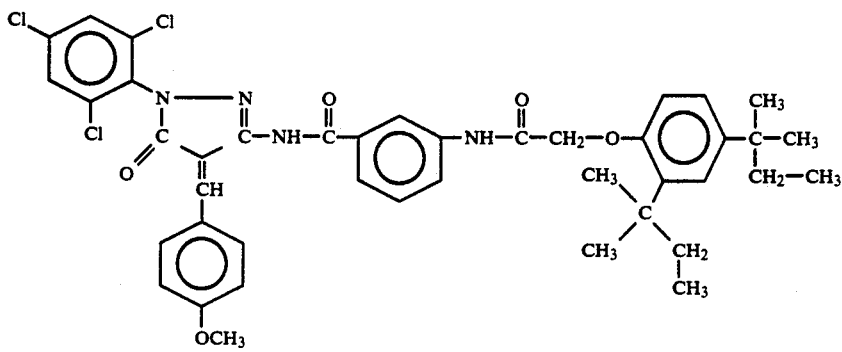
Example 20
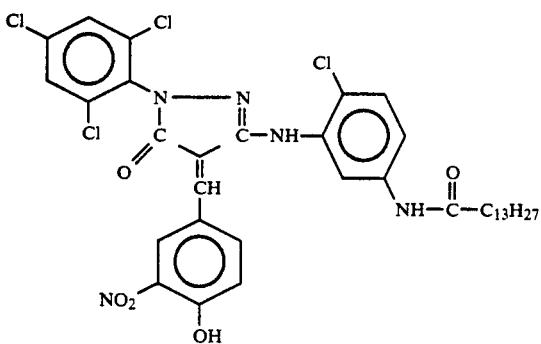
Example 21
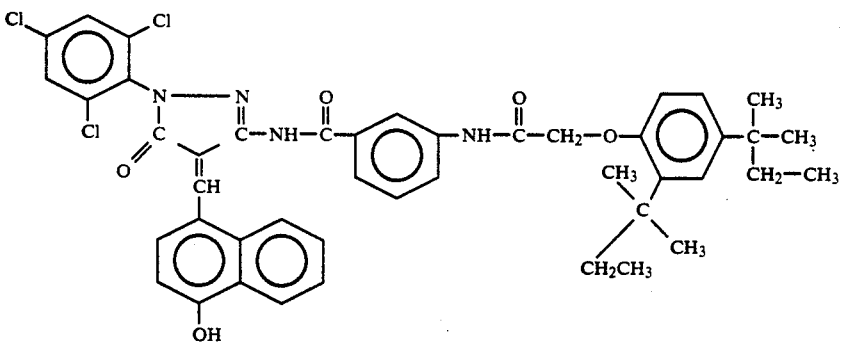
Example 22
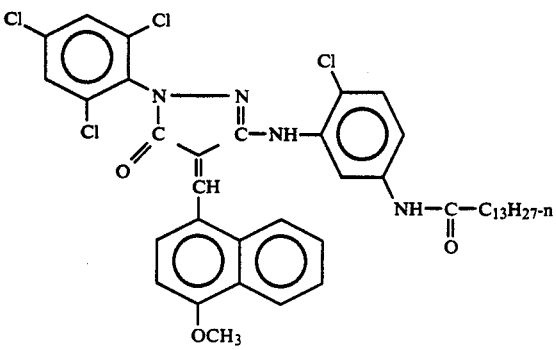
Example 23

-continued

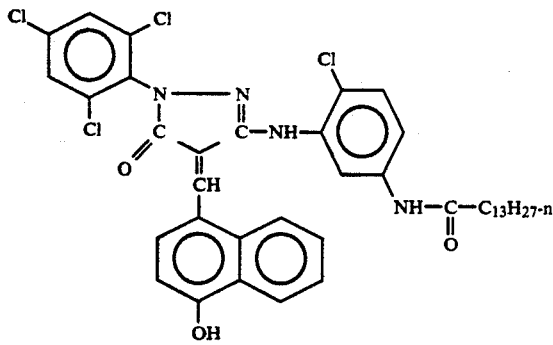

20

The foregoing examples and comparative examples can be incorporated into single layer silver halide photographic elements by coating a cellulose acetate-butyrate film support with a photosensitive layer containing a silver bromoiodide emulsion at 84.2 mg/ft², gelatin at 350 mg/ft² and the arylidene pyrazolone compound at 0.10 mmol/ft². The photosensitive layer was overcoated with a layer containing gelatin at 250 mg/ft² and bis-vinylsulfonyl methyl ether hardener at 1.75 weight percent based on total gel.

Single layer silver halide photographic elements having the above format and including compounds according to the present invention having structures represented by Examples 1 and 20-24, respectively, were exposed imagewise through a stepped density test object and processed at 100° F. employing the following color developing solution, then stopped with a low pH bath, bleached, fixed, washed, and dried to produce stepped colored images.

Color Developing Solution:
800.0 ml water;
34.30 g potassium carbonate, anhydrous;
2.32 g potassium bicarbonate;
0.38 g sodium sulfite, anhydrous;
2.78 g sodium metabisulfite;
1.20 mg potassium iodide;
1.31 g sodium bromide;
8.43 g diethylenetriaminepentaacetic acid pentasodium salt (40% solution);
2.41 g hydroxylamine sulfate (HAS);
4.52 g KODAK Color Developing Agent CD-4 (sulfate salt (1:1) of 2-[(4-amino-3-methylphenyl)ethylamino] ethanol) represented by the formula below; and
1.00 L of water to make, 10.0 pH.

Example 24

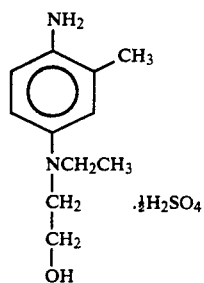

CD-4

For comparative purposes, photographic elements which each include a pyrazolone arylidene compound as shown below in Comparative Examples 1 and 2 were also exposed imagewise and processed as described above.

Comparative Example 1

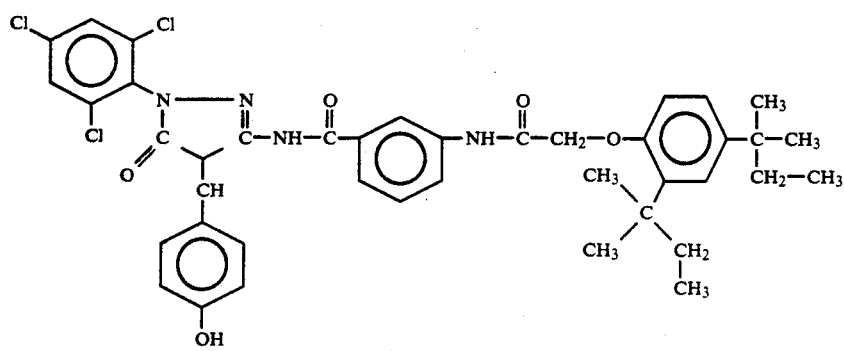

-continued

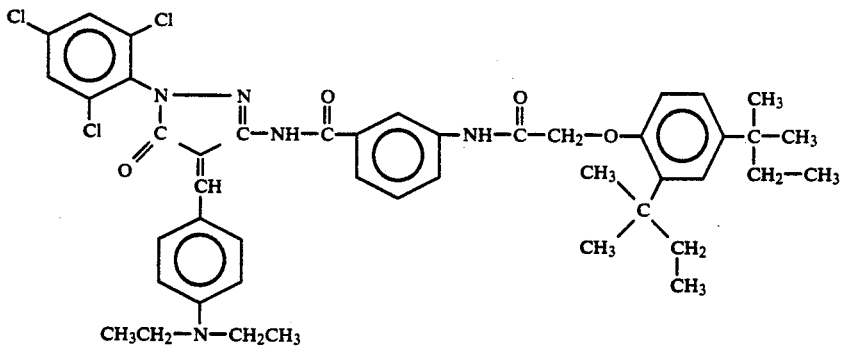

Comparative Example 2

Table 1 shows the blue density of the tested compounds prior and subsequent to processing without exposure. It is evident that Comparative Example 2 has blue density both before and after processing, thus indicating that it remains yellow-colored in the nonexposed areas. Image dye-forming coupler/filter dye Examples 1, 20 and 21, on the other hand, have a certain amount of blue density prior to processing but essentially no blue density after processing. This indicates that the original yellow color of these compounds is destroyed in the unexposed areas upon processing.

Table 1 also shows the green and blue densities of the tested compounds at minimum and maximum exposure. Examples 1 and 20-24 have a high green density at maximum exposure, indicating the occurrence of coupling and the resulting formation of a magenta dye image, and a low green density at minimum exposure, indicating the lack of a magenta dye and thus no coupling. Masking coupler Examples 22-24 have a high blue density at minimum exposure and a low blue density at maximum exposure, indicating that the yellow color of the masking coupler as coated is destroyed imagewise. The image dye-forming coupler/filter dye Examples 1, 20 and 21 have a higher blue density at maximum exposure since the magenta dye that is formed imagewise has an unmasked blue side-absorbance.

TABLE I

| Compound | Raw Stock Blue Density[a] | Blue Density After Process[b] | Blue Density[c] | | Green Density[c] | |
|---|---|---|---|---|---|---|
| | | | $E_{min}$ | $E_{max}$ | $E_{min}$ | $E_{max}$ |
| Example 1 (F) | 0.05 | 0.00 | 0.05 | 0.21 | 0.05 | 0.73 |
| Example 20 (F) | 0.07 | 0.00 | 0.07 | 0.16 | 0.05 | 0.48 |
| Example 21 (F) | 0.10 | 0.00 | 0.14 | 0.54 | 0.07 | 2.48 |
| Example 22 (M) | 0.75 | 0.75 | 0.81 | 0.29 | 0.14 | 0.51 |
| Example 23 (M) | 1.65 | 1.65 | 1.70 | 1.54 | 0.23 | 1.00 |
| Example 24 (M) | 2.25 | 2.25 | 2.03 | 1.72 | 0.27 | 1.53 |
| Comparative Example 1 | 0.00 | 0.00 | 0.05 | 0.05 | 0.04 | 0.05 |
| Comparative Example 2 | 1.38 | 1.38 | 0.93 | 0.98 | 0.18 | 0.51 |

[a]Status M Blue Density of untreated raw stock (no process, contains silver) corrected for Status M Blue Density of the support plus silver (no coupler) control.
[b]No exposure; corrected for Blue $D_{min}$ of the support
[c]$E_{min}$ = minimum exposure; $E_{max}$ = maximum exposure; uncorrected
F Image dye-forming coupler/filter dye according to present invention
M Masking coupler according to present invention The invention has been described in detail with particular reference to certain preferred embodiments thereof, but it will be understood that variations and modifications can be effected within the spirit and scope of the invention.

What is claimed is:

1. A photographic element comprising a support bearing a silver halide photographic emulsion and yellow-colored image dye-forming coupler, wherein said image dye-forming coupler is a ballasted arylidene pyrazolone which is also a filter dye that upon exposure and processing of said element is destroyed in both exposed and unexposed ares of said element or a masking coupler that upon exposure and processing is destroyed only in exposed areas of said element, and wherein said image dye-forming coupler is represented by the formula A:

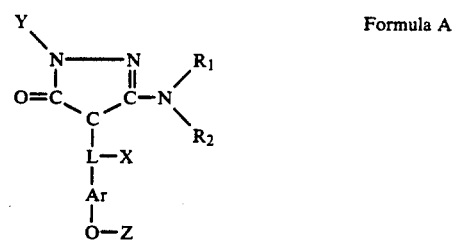

Formula A wherein
L is an alkenyl or alkadienyl group and Ar is a substituted aromatic group having the —O—Z group in conjunction with L and optionally having additional substituents;
X is a hydrogen atom, a branched or unbranched aliphatic group or a heterocyclic ring formed with Ar;
Y is an unsubstituted aryl group, or an aryl or pyridyl group substituted with at least one substituent selected from the group consisting of a halogen atom and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl and trifluoromethyl groups;
Z is a hydrogen atom, an alkyl group, an aryl group or an arylalkyl group;
$R_1$ represents a substituted or unsubstituted aromatic group or a substituted or unsubstituted aromatic or aliphatic carbonyl group, and $R_2$ is a hydrogen atom, a substituted or unsubstituted aromatic group, a branched or unbranched aliphatic group, a heterocyclic group, a substituted or unsubstituted aromatic or aliphatic carbonyl group, a substituted or unsubstituted aromatic or aliphatic sulfonyl group, or a substituted or unsubstituted aromatic or aliphatic sulfamoyl group; and
at least one of Ar, X, Y, Z, $R_1$ and $R_2$ includes a ballast group which renders the arylidene pyrazolone substantially immobile.

2. A photographic element according to claim 1, wherein said arylidene pyrazolone is a filter dye and Ar is a substituted phenyl group.

3. A photographic element according to claim 1, wherein said arylidene pyrazolone is a masking coupler and Ar is a substituted naphthyl group.

4. A photographic element according to claim 1, wherein said -O- Z group is positioned para to L.

5. A photographic element according to claim 1, wherein Z is a hydrogen atom.

10. A photographic element according to claim 1, wherein the total number of carbon atoms in $R_1$ and $R_2$ is at least 6.

11. A photographic element according to claim 1, wherein at least one of Ar, X, Y, Z, $R_1$ and $R_2$ further includes a solubilizing group selected from the group consisting of carboxyl, sulfonic and sulfonamide groups.

12. A photographic element according to claim 1, wherein said image dye-forming coupler is a compound represented by the formula I:

FORMULA I

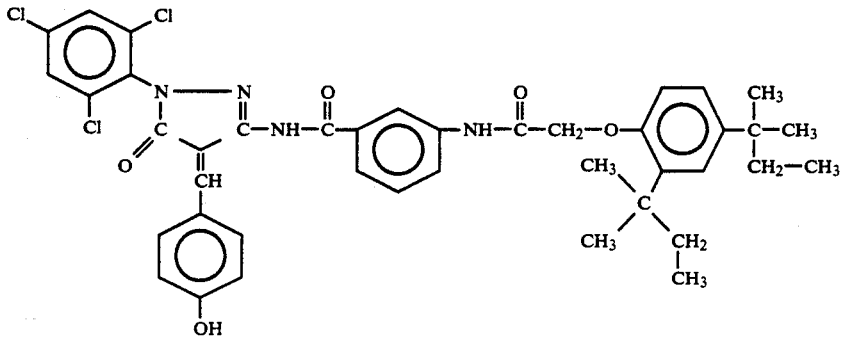

6. A photographic element according to claim 1, wherein Ar is substituted at a position meta to L with a substituent selected from the group consisting of a carbamoyl group, a sulfamoyl group, a sulfonyl group, a nitro group and an azo group.

7. A photographic element according to claim 1, wherein X is a hydrogen atom.

8. A photographic element according to claim 1, wherein Y is a substituted aryl group selected from the group consisting of a 2,4,6-trichlorophenyl group, a 2,5-disubstituted aryl group and a 2,6-disubstituted aryl group, $R_1$ is a hydrogen atom, and $R_2$ is selected from the group consisting of a substituted aromatic group and a substituted aromatic carbonyl group.

9. A photographic element according to claim 1, wherein L is a methine group.

13. A photographic element comprising an image dye-forming coupler according to claim 1 and a support bearing at least one blue-sensitive silver halide emulsion layer, at least one green-sensitive silver halide emulsion layer and at least one red-sensitive silver halide emulsion layer.

14. A photographic element comprising a masking coupler according to claim 3 and a support bearing at least one blue-sensitive silver halide emulsion layer, at least one green-sensitive silver halide emulsion layer and at least one red-sensitive silver halide emulsion layer, wherein said masking coupler is coated with said green-sensitive silver halide emulsion layer.

15. A process of forming a photographic image which comprises developing an exposed photographic element according to claim 13 with a color developing agent.

* * * * *